United States Patent [19]

Ciaudelli

[11] Patent Number: 5,139,784
[45] Date of Patent: Aug. 18, 1992

[54] ALKYL DIAMIDES AND COSMETIC TREATING COMPOSITIONS THEREWITH

[75] Inventor: Joseph P. Ciaudelli, Ramsey, N.J.

[73] Assignee: Revlon, Inc., New York, N.Y.

[21] Appl. No.: 493,080

[22] Filed: Mar. 13, 1990

[51] Int. Cl.$^5$ .................. A61K 7/02; A61K 7/48; A61K 31/16

[52] U.S. Cl. ................ 424/401; 424/59; 424/63; 424/64; 514/563; 514/616; 514/625; 514/844; 514/873; 514/847

[58] Field of Search ............ 424/63, 64; 514/563, 514/616, 625, 788, 847, 873

[56] References Cited

U.S. PATENT DOCUMENTS

| | | | |
|---|---|---|---|
| 3,025,323 | 3/1962 | Rose | 564/159 |
| 3,766,267 | 10/1973 | Zak | 564/201 |
| 3,855,290 | 12/1974 | Zak | 564/159 |
| 4,038,294 | 7/1977 | Conner | 260/404.5 |
| 4,076,799 | 2/1978 | Willer et al. | 514/616 X |
| 4,105,783 | 8/1978 | Yu | 514/459 |
| 4,143,159 | 3/1979 | Moller et al. | 514/788 |
| 4,197,316 | 4/1980 | Yu | 424/317 |
| 4,529,588 | 7/1985 | Smith | 424/70 |
| 4,534,964 | 8/1985 | Herstein | 424/70 |
| 4,912,135 | 3/1990 | Taguchi et al. | 514/616 X |

FOREIGN PATENT DOCUMENTS 2338087 1/1975 Fed. Rep. of Germany.

OTHER PUBLICATIONS

Starch, vol. 33, No. 6 (1981), p. 202, Emmerling.
Journal of Dairy Science, vol. 63, pp. 471-473 (1988), Sholnik.
Inorganica Chemica Arta 106 (1985) pp. 203-208.
C. R. Acad. Sc. Paris t.301 Serie III no 1, 1985, Masse'.
Analytical Biochemistry 130, 485-490 (1983) Hjelmeland.

Primary Examiner—Thurman K. Page
Assistant Examiner—James M. Spear
Attorney, Agent, or Firm—Julie Blackburn

[57] ABSTRACT

Comsetic compositions containing alkyl diamides for use in providing moisturizing and/or softening properties to treat dry human skin and for use in other cosmetic applications and including also various novel alkyl diamides.

6 Claims, No Drawings

ALKYL DIAMIDES AND COSMETIC TREATING COMPOSITIONS THEREWITH

FIELD OF THE INVENTION

The present invention relates to alkyl diamides, including novel alkyl diamides, and to the use of such compounds in cosmetic compositions.

The invention will be described initially in connection with its use to provide moisturizing and/or softening properties to dry skin. However, as described hereafter, the cosmetic composition of the present invention can be used advantageously for other types of cosmetic applications.

The human skin disorder known as "dry skin" is characterized by cracking, flaking or scaling of the skin of the hands, feet, neck, face or other parts of the body. This disorder may result from a hereditary disorder known as ichthyosis which is a severe form of dry skin. This form of dry skin is uncommon. The more common form of "dry skin," which affects a relatively large portion of the population, is a mild to moderate form of dry skin caused in large part by exposure to environmental conditions such as low humidity, wind and sun, or by exposure to substances which tend to dry the skin, such as detergents and various chemicals. These environmental conditions cause a loss of moisture from exposed skin areas, with the attendant formation of fissures, chaps, cracks or flakes in such affected skin areas.

The present invention relates to alleviating a dry skin condition by use of a compound which is applied to the skin.

REPORTED DEVELOPMENTS

Various compounds, including, for example, amides, have been proposed for use in combating such dry skin conditions. Such compounds are normally formulated with other materials so as to be useful for topical application to the skin in the form of a lotion, cream or ointment.

Examples of amides that have been disclosed for such use and the topical cosmetic compositions which contain them are disclosed, for example, in U.S. Pat. No(s). 3,230,228; 3,322,635; 4,038,294; 4,105,783; 4,197,316; 4,529,588; and 4,534,964. Diamides and topical cosmetic compositions which contain them are disclosed in U.S. Pat. No(s). 3,766,267 and 3,855,290 and in W. German OLS 2,632,391.

The present invention relates to the provision of novel cosmetic compositions based on alkyl diamides, including known and/or novel alkyl diamides, which are useful for a variety of cosmetic purposes, including the treatment of dry skin, particularly skin which is mildly to moderately dry.

SUMMARY OF THE INVENTION

In accordance with the present invention, there is provided a cosmetic composition which can be used to treat dry skin or for other cosmetic purpose and which comprises an alkyl diamide.

One aspect of the present invention comprises a cosmetic composition having, as one of its essential constituents, one or more alkyl diamides of the general structure

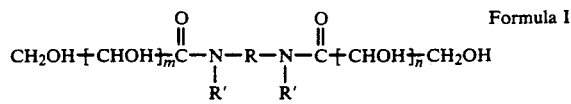

wherein m and n are independently whole numbers from 0 to about 4, R is a substituted or unsubstituted hydrocarbon selected from the group consisting of aryl and alkyl radicals containing from about 2 to about 14 carbon atoms and each R' is independently hydrogen or C1 to C4 alkyl. For convenience, compounds within the scope of Formula I above are hereafter sometimes referred to as "alkyl diamides." The cosmetic composition of the present invention includes also as an essential constituent a material, hereafter referred to as "a carrier," which is effective in providing an alkyl diamide-containing composition in a form such that the composition can be applied to the body, for example, the skin.

Another aspect of the present invention comprises novel alkyl diamide compounds having the general structure

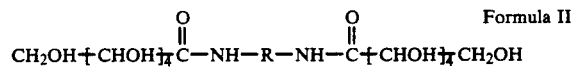

wherein R comprises a hydrocarbon selected from the group consisting of aryl and alkyl radicals containing from about 2 to about 14 carbon atoms. Such compounds are referred to herein as "bisgluconamides."

A preferred bisgluconamide of the present invention is N,N-1,3-propanediyl-2-hydroxybisgluconamide and has the following structure.

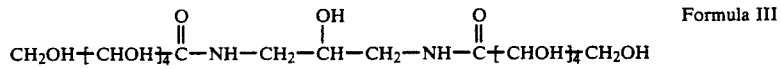

The preferred bisgluconamide exhibits unusually good properties in the cosmetic composition of the present invention, as will be discussed more fully below.

Another aspect of the present invention comprises a process in which one or more compounds of the present invention are applied to a portion of the body for the purpose of cosmetically treating said body portion, for example, for moisturizing and softening the human skin.

The term "cosmetic composition" is used herein in its usually understood sense, that is, to define a composition which is applied to a portion of the body, typically a human body, for beautifying, cleansing, moisturizing or otherwise treating the body, including by cleansing, coloring, conditioning, or protecting the surface of the body part, such as, for example, the skin and hair. Examples of cosmetic compositions in which the alkyl diamides of the present invention can be used are skin moisturizers, sun screens, makeup, protein concentrates, cleansers, including decongestant cleansers, and skin-firming compositions.

Advantages associated with compounds of the present invention are many. Novel alkyl diamides of the present invention have a neutral pH, enabling the use of a neutral pH carrier. Most prior art moisturizers, such as aliphatic hydorxyacids, are acidic, and must be neutralized or incorporated into a basic carrier to be effective and non-irritating to human skin. Alkyl diamides of the present invention are also easily handled and stored, as they can be prepared in the form of a chemically stable, plain white powder. In addition, compounds of the present invention are water-soluble, enabling them to be incorporated easily into water-based compositions. They can also be easily manufactured by known methods from readily available precursors.

DETAILED DESCRIPTION OF THE INVENTION

As mentioned above, the essential ingredients of the cosmetic compositions of the present invention are one or more of the alkyl diamides of Formula I above and a carrier therefor. For many applications, the composition will include one or more additional ingredients, the identity of which will depend on the intended use of the composition and the selection of which can be made in accordance with available knowledge in the art.

With reference to the alkyl diamide constituent, as set forth above, "R" of Formulae I and II can comprise a substituted or unsubstituted aryl or alkyl group containing from about 2 to about 14 carbon atoms. Examples of aryl groups are phenylene, naphthylene, phenanthrylene and anthracenylene. If alkyl, R can be straight or branched chain. Each of the aryl and alkyl groups can be substituted with groups such as hydroxy, alkoxy and carbonyl.

The preferred alkyl group for R is propylene. Most preferably, R is 2-hydroxypropylene.

R' of Formula I above can be either hydrogen or C1 to C4 alkyl. If alkyl, R' can be straight or branched chain. Preferably, R' is hydrogen.

The alkyl diamides of Formula I can be prepared by any suitable method.

In preferred form, the Formula I compounds of the present invention are prepared by reacting one mole of a diamino compound having the structure

$$\begin{array}{cc} R' & R' \\ | & | \\ HN-R-NH \end{array} \quad \text{Formula IV}$$

with two moles of a carboxylic acid or lactone having one of the structures

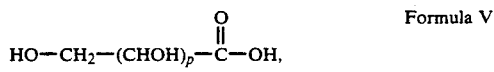
$$HO-CH_2-(CHOH)_p-\overset{O}{\overset{\|}{C}}-OH, \quad \text{Formula V}$$

or

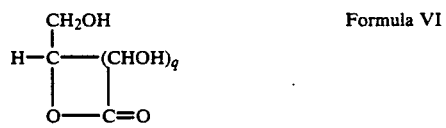
Formula VI wherein R and R' are as defined in Formula I, p is a whole number from 0 to 4, and q is a whole number from 1 to 3.

For use in preparing the preferred compound of Formula III, the Formula IV diamino compound is 1,3-diamino-2-hydroxypropane, the Formula V carboxylic acid is gluconic acid, that is, wherein p is 4, and the Formula VI lactone is glucono-delta-lactone, that is, wherein q is 3.

The lactone/acid is first heated with stirring in a refluxing alcoholic solvent, at atmospheric pressure, to slurry the solids. The alcohol used is aliphatic and has a reflux temperature of about 65 to about 86° C. The amine is added dropwise to the slurry, in the refluxing solvent. As the reaction progresses, a precipitate forms in the solvent. After about 10 to 30 minutes at reflux temperatures, heating is discontinued and the solution is allowed to cool with stirring. Upon reaching room temperature (−25° C.), the solids are filtered off under vacuum and air dried. Yields of about 90 to about 99% of the diamides are thus obtained after drying.

The carrier for use in formulating the composition of the present invention can comprise one or more compounds which will be selected based on the particular intended use of the composition. Speaking generally, the carrier functions to permit formulation of a composition that allows the alkyl diamide to be applied to a body surface in the desired way. The carrier may be inorganic or organic in nature, and like the alkyl diamide, it must be non-toxic and non-irritating and should also be inoffensive to the user. The carrier must, of course, be compatible with the alkyl diamide. Examples below are illustrative of a variety of carriers that can be used.

In addition to the essential ingredients described above, the composition of the present invention can include also one or more optional ingredients, also referred to herein as "auxiliary components." Examples of auxiliary components are lubricants, preservatives, perfumes and colorants.

Examples of carriers and auxiliary components, which are well known in the art, are disclosed, for example, in "Cosmetics: Science and Technology," Edited by M. S. Balsam and E. Sagarin, 2nd Edition, 1972, Wiley Pub. Co.; "The Chemistry and Manufacture of Cosmetics," M. G. DeNavasse; and "Harry's Cosmeticology," J. B. Wilkinson et al., 7th Edition, 1982, Chem. Pub. Co., the disclosures of each of the above being incorporated herein by reference.

It is believed that the composition of the present invention will be used most widely in applications that are designed for use in treating humans having a dry skin condition. Accordingly, at least one of the active ingredients used in such compositions for such purposes will comprise one or more of the Formula I compounds defined above, and most preferably the compound of Formula III.

The composition of the present invention may be used for prophylactic as well as therapeutic purposes, relative to their proposed use in treating dry skin by the topical application thereto, so as to prevent or cure the occurrence of any cracking, flaking, scaling or chapping of the skin. Thus, compositions of the present invention may be used to prevent, cure, or ameliorate dry skin conditions, acne, psoriasis, seborrhea, keratose, diaper rash, sunburn and windburn.

Compositions of the present invention may be prepared and used in the form of a lotion, cream, ointment, stick, soap, or other form commonly employed in the cosmetic art, including skin care formulations. They are preferably used in an emulsified form.

For use in treating dry skin, compositions of the present invention are prepared employing skin-softening and moisturizing effective amounts (for example, up to about 25 wt. %) of one or more of the alkyl diamide compounds of the present invention in a cosmetically acceptable carrier, such as a hydrophilic ointment (USP) or petrolatum. When used in such compositions, preferably about 1 to about 20 wt. %, and most preferably about 5 to about 15 wt. % of the alkyl diamide compound(s) is used therein. It should be understood that smaller amounts of the alkyl diamide can be used in compositions within the scope of the present invention, for example, in compositions which include one or more other skin-moisturizers or softeners or when used in compositions that are designed primarily for other types of cosmetic functions. This is discussed more fully below.

When an aqueous carrier is utilized, the bulk of such compositions of the present invention will comprise about 30 to about 75 wt. %, and preferably about 55 to about 65 wt. % of distilled water, and about 10 to about 40 wt. %, and preferably about 15 to about 30 wt. %, of a combination of other commonly used cosmetically effective auxiliary components of the various types of compositions in question (for example, a lotion, cream, ointment, stick or soap). It should be understood, however, that the water in the composition can be at least partly eliminated by the use of non-aqueous carriers, for example, hydrocarbons. Typically, the auxiliary components are chemically inert with respect to each other, and with respect to the alkyl diamide compounds of the present invention.

In accordance with the present invention, the following is particularly recommended for use as an aqueous composition in dry skin applications (weight %, based on total weight of the composition):

about 1 to about 25% diamide(s) of the present invention
about 0.75 to about 7% emulsifying agent(s)
about 3 to about 15% emollient(s)
about 0.1 to about 5% lubricant(s)
about 0.2 to about 1% preservative(s)
about 0.2 to about 1% perfume(s)
about 0.01 to about 0.1% colorant(s)
remainder, water.

Although it is believed that the present invention will be practiced most widely by use of a formulation containing the alkyl diamide compound, it should be understood that the compound can be topically applied cosmetically in uncompounded form to the areas of the skin to be treated therewith.

Whether used in neat form (e.g. as a pure compound or in aqueous solution), or in compounded or compositional form, for dry skin-treating purposes, the alkyl diamide compound of the present invention can be topically applied one or more, and preferably about 2 to 4, times per day to the area of skin to be treated therewith for a period of time sufficient to achieve the desired amelioration of the dry skin condition, for example, about 7 to about 21 days.

As mentioned above, the alkyl diamides can be used effectively also in applications that are designed primarily to treat conditions other than dry skin conditions, for example, in makeup, cleansers, sunscreens, self-tanning and lightening compositions, skin firmers, shaving preparations, shampoos, topically applied therapeutic compositions and depilatories. It is believed that the alkyl diamides will be used most widely in relatively small amounts.

Makeup compositions, for example, can effectively incorporate the alkyl diamide in small amounts, generally about 0.01 wt. % to about 5 wt. %, preferably about 0.02 wt. % to about 0.1 wt. % of the composition. In addition, makeup compositions of the present invention generally comprise about 1 to about 40 wt. %, preferably about 10 to about 20 wt. % of a coloring agent (for example pigment) in a suitable carrier. Suitable pigments include all inorganic and organic pigments which are usable in cosmetic formulations. Examples include carmine, bismuth oxychloride, zinc oxide, ferric oxide, ferrous oxide, kaolin, ultramarine violet, ultramarine blue, chromium oxide, chromium hydroxide, silica and manganese violet. Other examples include lakes of organic colorants such as FD&C Red No. 7 calcium lake, FD&C Yellow No. 5 aluminum lake, FD&C Red No. 9 barium lake and FD&C Red No. 30. Additional examples include talc, mica, and titanium oxide; any of the foregoing carried on the surface of talc, mica or tatanium oxide; and titanated mica. Unless stated a mixture of two or more pigments.

Compounds of the present invention may be stored effectively in neat form or in the form of a cosmetic formulation in closed containers at room temperature for extended periods of time.

Examples set forth below show the use of the alkyl diamides in various types of cosmetic compositions. The examples are illustrative of the present invention and are not intended as a limitation upon the scope thereof.

EXAMPLES

The first example shows the preparation of the preferred bisgluconamide of the present invention.

EXAMPLE NO. 1

Glucono delta lactone (89.07 grams) was heated in isopropyl alcohol (200 grams) to reflux temperatures (about 86° C. at atmospheric pressure) in a flask equipped with a stirrer and reflux condenser column. 1,3-Diamino-2-hydroxypropane (22.53 grams, dissolved in 50 grams isopropyl alcohol) was added dropwise to the refluxing lactone slurry over a period of about 15 minutes. During this period, a milky white suspension was produced as a precipitate formed. An additional 200 grams of isopropyl alcohol and 200 ml of water were slowly added.

The resulting mixture was then stirred and allowed to cool. When the temperature of the mixture reached ambient temperature ($-25°$ C.), the precipitate was filtered off under vacuum and air dried. A yield of 104 grams of product (N,N-1,3-propanediyl-2-hydroxybisgluconamide) was obtained. This was a yield of 93.2% of the theoretical.

An analysis of the product showed that it contained 5.86% nitrogen, as compared to 6.28% theoretical. The compound melted between 180 and 184° C.

The reaction was repeated using methanol as the solvent. A yield of 106 grams, 95% of the theoretical, was obtained. The product contained 6.13% nitrogen and melted between 183 and 186° C.

The next group of examples are illustrative of other bisgluconamides of the present invention.

EXAMPLE NOS. 2 to 5

Using procedures similar to that described above, the following compounds, listed in Table 1 below, were made.

TABLE 1

| Ex. No. | Compound Name (all are -bisgluconamides) | m.p. (°C.) | N Content, % (calc.) | N Content, % (found) |
|---|---|---|---|---|
| 2 | N,N-1,3-propanediyl- | 165–170 | 6.50 | 6.40 |
| 3 | N,N-1,6-hexanediyl- | 180–183 | 5.93 | 5.70 |
| 4 | N,N-1,5-anthraquinone- | 200 (dec.) | 4.71 | 4.54 |

TABLE 1-continued

| Ex. No. | Compound Name (all are -bisgluconamides) | m.p. (°C.) | N Content, % (calc.) | (found) |
|---|---|---|---|---|
| 5 | N,N-1,12-dodecanediyl- | 187–193 | 5.03 | 4.98 |

The following examples are illustrative of cosmetic compositions within the scope of the present invention and include the results of evaluations thereof.

EXAMPLE NOS. 6 and 7

The following skin cream formulations containing bisgluconamides within the scope of the present invention were formulated. Table 2 below identifies the ingredients for the compositions of Examples 6 and 7.

TABLE 2

| Ingredient (wt. %) | Ex. No. 6 | Ex. No. 7 |
|---|---|---|
| N,N-1,3-propanediyl-2-hydroxybisgluconamide | 5 | — |
| N,N-1,3-propanediylbisgluconamide | — | 5 |
| Methyl Paraben | 0.25 | 0.25 |
| Propylene glycol | 5 | 5 |
| Guar hydroxy propyltrimonium Cl | 1.5 | 1.5 |
| Glyceryl stearate, Laureth-23 | 8 | 8 |
| Cetyl alcohol | 1.5 | 1.5 |
| Propylparaben | 0.15 | 0.15 |
| Butylated hydroxyanisole | 0.15 | 0.15 |
| $C_{12-15}$ alcohols benzoate | 5 | 5 |
| Isocetyl linoleoyl oxystearate | 5 | 5 |
| Bisabolol | 0.2 | 0.2 |
| Glycol stearate/other ingredients | 3 | 3 |
| Polyoxyethylene 21 stearyl ether | 0.75 | 0.75 |
| Dimethicone | 1 | 1 |
| Octyldimethyl PABA | 7 | 7 |
| Benzophenone-3 | 3.5 | 3.5 |
| DMDM Hydantoin | 0.4 | 0.4 |
| Perfume | 0.25 | 0.25 |
| Water | 52.35 | 52.35 |
| Total | 100.00 | 100.00 |

The above formulations are useful for treating dry skin and protecting against solar radiation.

EXAMPLE NOS. 8 to 11

Four cosmetic compositions, each containing a different bisgluconamide of the present invention, were formulated and comparatively evaluated as skin-moisturizing agents. Each composition was prepared according to the compositions described in Table 2 above, except that the $C_{12-15}$ alcohols benzoate component was replaced by hydrogenated polybutenes. Each of the compositions contained 5% of the bisgluconamide identified in Table 3 below.

Test panelists each applied one composition to their forearms twice daily over a period of two weeks. Skin moisture content, as measured by electrical conductivity of the skin, was measured before the test, at the end of each week during sample use, and daily for the three days after cessation of use. The results, shown below in Table 3 below, are mean values based on a value of 1 for the initial skin conductivity measurements.

TABLE 3

| Ex. No. | Compound Tested | Testing Week 1 | Testing Week 2 | Regression Day 1 | Regression Day 2 | Regression Day 3 |
|---|---|---|---|---|---|---|
| 8 | N,N-1,12-Dodecanediyl-bisgluconamide | 3.97 | 3.78 | 2.95 | 1.44 | 1.05 |
| 9 | N,N-1,3-Propanediyl-bisgluconamide | 4.11 | 3.27 | 1.63 | 2.02 | 2.06 |
| 10 | N,N-1,3-Propanediyl-2-hydroxybisgluconamide | 6.53 | 8.58 | 4.01 | 3.81 | 1.97 |
| 11 | N,N-1,6-Hexanediyl-bisgluconamide | 5.93 | 3.52 | 3.69 | 1.57 | 1.92 |

The above results show that the compositions of the present invention are effective in raising the moisture content of skin, as measured by electrical conductivity. Each of the tested compositions increased skin conductivity at least about four-fold after one week of regular use. A second week of continuous use yielded comparable measurements. After two weeks, use of the compositions was terminated and skin conductivity was measured after each of the first three days of non-use. As would be expected, skin conductivity levels dropped after use of the compositions ceased. After three days, however, skin conductivity was still about double the initial (before topical application began) levels, for three of the tested compositions (Examples 9, 10 and 11). This shows that the moisturizing properties of the composition of the present invention are relatively long-lasting.

In summary, it can be said that the present invention affords the means for providing improved cosmetic compositions which can be tailor-made into a variety of different types of formulations to suit particular needs.

What is claimed is:

1. A cosmetic composition comprising 0.01–25% of the reaction product prepared by reacting one mole of a diamino compound of the formula:

with two moles of a compound selected from the group consisting of:

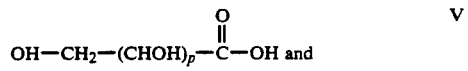

wherein R is a substituted or unsubstituted hydrocarbon selected from the group consisting of aryl and alkyl radicals containing from about 2 to about 14 carbon atoms, R' is each independently H or $C_{1-4}$ alkyl, p is 0–4, and q is 1–3, wherein said reaction comprises the steps of
   (a) stirring the Formula V or VI compound in a reflux aliphatic alcohol solvent at atmospheric pressure and a temperature of 65°–86° C. to slurry the solids,
   (b) adding the Formula IV compound to the slurry while stirring, (c) cooling the solution,
(d) filtering off and drying the solids to yield the reaction product.

2. The cosmetic composition of claim 1 wherein the reaction product is of the formula:

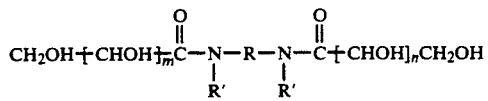

wherein R and R' are as in claim 1 and m and n are each independently whole numbers from 0–4.

3. The cosmetic composition of claim 2 wherein the reaction product is of the formula:

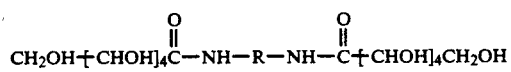

4. The cosmetic composition of claim 3 wherein the reaction product is selected from the group consisting of:
N,N-1,3-propanediyl bisgluconamide
N,N-1,6-hexanediyl bisgluconamide
N,N-1,5-anthroquinone bisgluconamide
N,N-1,12-dodecanediyl bisgluconamide
N,N-1,3-propanediyl-2-hydroxybisgluconamide.

5. The cosmetic composition of claim 4 wherein the reaction product if N,N-1,3-propanediyl-2-hydroxybisgluconamide.

6. A method for the manufacture of a compound of the formula:

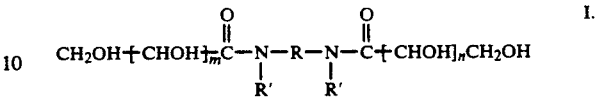

wherein R is a substituted or unsubstituted hydrocarbon selected from the group consisting of aryl and slkyl radicals containing from about 2 to 14 carbon atoms, and m and n are each independently whole numbers from 0–4; comprising the steps of:
(a) stirring a compound selected from the group consisting of a Formula V or Formula VI compound in a reflux aliphatic alcohol solvent at atmospheric pressure and a temperature of 65°–85° C. to slurry the solids,
(b) adding a compound of the Formula IV to the slurry and stirring,
(c) cooling the solution,
(d) filtering off and drying the solids to yield the product.

* * * * *